(12) United States Patent
Gelke

(10) Patent No.: US 12,232,797 B2
(45) Date of Patent: Feb. 25, 2025

(54) ELECTROSURGICAL SYSTEM AND METHOD FOR OPERATING AN ELECTROSURGICAL SYSTEM

(71) Applicant: OLYMPUS WINTER & IBE GMBH, Hamburg (DE)

(72) Inventor: Marius Gelke, Stahndorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 518 days.

(21) Appl. No.: 17/684,086

(22) Filed: Mar. 1, 2022

(65) Prior Publication Data
US 2022/0273354 A1 Sep. 1, 2022

(30) Foreign Application Priority Data
Mar. 1, 2021 (DE) .................. 10 2021 104 872.9

(51) Int. Cl.
 *A61B 18/14* (2006.01)
 *A61B 18/12* (2006.01)
 *A61B 18/00* (2006.01)

(52) U.S. Cl.
 CPC .......... *A61B 18/1206* (2013.01); *A61B 18/14* (2013.01); *A61B 2018/00011* (2013.01); *A61B 2018/0016* (2013.01); *A61B 2018/00875* (2013.01); *A61B 2018/126* (2013.01); *A61B 2018/1467* (2013.01)

(58) Field of Classification Search
 CPC .. A61B 2018/1467; A61B 2018/00875; A61B 2018/00011; A61B 18/14; A61B 18/1206
 See application file for complete search history.

(56) References Cited

U.S. PATENT DOCUMENTS 6,522,930 B1 * 2/2003 Schaer ............... A61B 18/1492
607/104

FOREIGN PATENT DOCUMENTS

| DE | 20 2008 000 276 U1 | 5/2008 |
|---|---|---|
| DE | 10 2008 022 816 A1 | 11/2009 |
| DE | 10 2014 217 095 A1 | 3/2016 |
| DE | 10 2017 101 674 A1 | 8/2018 |
| DE | 102017101674 * | 8/2018 |
| EP | 2 143 394 A2 | 1/2010 |

* cited by examiner

*Primary Examiner* — Linda C Dvorak
*Assistant Examiner* — Ryan T Clark
(74) *Attorney, Agent, or Firm* — Oliff PLC

(57) ABSTRACT

An electrosurgical system includes a liquid feeding device for feeding a quantity of liquid to the distal end of a shaft of a bipolar electrosurgical instrument, an impedance measuring device for measuring the impedance of an object arranged at the distal end of the shaft, and a control device that is connected to the impedance measuring device and the liquid feeding device and is configured to control and/or dose the quantity of liquid fed by the liquid feeding device to the distal end of the shaft as a function of the measurement of the impedance measured by the impedance measuring device.

11 Claims, 1 Drawing Sheet

ELECTROSURGICAL SYSTEM AND METHOD FOR OPERATING AN ELECTROSURGICAL SYSTEM

TECHNICAL FIELD

The present disclosure relates to an electrosurgical system as well as a method for operating an electrosurgical system.

BACKGROUND

In high-frequency surgery, which is also referred to as HF surgery, a high-frequency alternating currency is conducted through tissue which is to be treated surgically in order, for example, to deliberately damage or cut said tissue. This surgical technique allows, inter alia, simultaneous cutting and hemostasis.

During high-frequency surgery, an electrode is attached to a surgical instrument, for example to a resectoscope. In order to operate the electrode, it is important that it is operated with the envisaged operating parameters. These operating parameters include, e.g., the voltage applied to the electrode. Depending on the type of electrode, different voltage values are to be adjusted.

An electrosurgical system usually comprises a HF generator having a rating of several 100 Watts and an operating voltage of 1000 Volts and more. A HF signal produced by the HF generator is applied to the HF electrode. During bipolar HF surgery, the HF instrument deployed for the treatment comprises two poles, between which the current produced by the HF generator flows.

Bipolar electrosurgical instruments are deployed for ablation or coagulation of biological tissue. In order to treat the tissue, the bipolar electrosurgical instrument is guided into a lumen of the body, for example into the liver, wherein the two electrodes are supplied with a high-frequency voltage.

The high-frequency voltage is provided by a high-frequency generator connected to the bipolar electrosurgical instrument. During the treatment which usually uses high-frequency currents (approx. 0.2 MHz to 3 MHz), the high-frequency current flows from the one electrode via the tissue to be treated to the other electrode of the bipolar electrosurgical instrument.

SUMMARY

It is an object of the present disclosure to provide an electrosurgical system and a method for operating an electrosurgical system, wherein, e.g., during an application to coagulate the tissue the application of the system is to be simplified.

This object is achieved by an electrosurgical system,
  having a bipolar electrosurgical instrument, wherein the bipolar electrosurgical instrument has an elongated shaft with a proximal end and a distal end, and a first electrode and a second electrode are provided at the distal end of the shaft, wherein the first electrode is connected to a first electrical conductor and the second electrode is connected to a second electrical conductor, and having a high-frequency generator, wherein a first output contact of the high-frequency generator can be or is connected to the first electrical conductor of the bipolar electrosurgical instrument and a second output contact of the high-frequency generator can be or is connected to the second electrical conductor of the bipolar electrosurgical instrument,
  wherein a liquid feeding device for feeding a quantity of liquid to the distal end of the shaft of the bipolar electrosurgical instrument is provided,
  wherein the distal end of the shaft of the bipolar electrosurgical instrument has at least one outlet opening for the passage of the quantity of liquid fed by the liquid feeding device to the distal end of the shaft of the bipolar electrosurgical instrument out of the distal end of the shaft of the bipolar electrosurgical instrument,
  wherein an impedance measuring device for measuring the impedance of an object arranged at the distal end of the shaft of the bipolar electrosurgical instrument is provided,
  wherein a control device is connected to the impedance measuring device and the liquid feeding device such that the quantity of liquid fed by the liquid feeding device to the distal end of the shaft of the bipolar electrosurgical instrument is dosed and/or controlled as a function of the, in particular current, measurement of the impedance of the high-frequency generator measured by the impedance measuring device.

The disclosure is based on the idea that during the treatment, e.g., of biological tissue using the bipolar electrosurgical instrument, the tissue impedance of the high-frequency generator is measured or captured by means of the impedance measuring device, as a result of which liquid is dispensed in a dosed and/or controlled manner on the basis of the control circuit according to the disclosure having the control device into the surroundings of the object to be treated or of the biological tissue such that a defined predetermined, in particular optimal quantity of conductive liquid is provided, for example, for each phase of a tissue coagulation, as a result of which the impedance of the tissue is or will be stabilized. In this respect, it is guaranteed that during the application of the bipolar electrosurgical instrument, e.g., for coagulating tissue, sufficient electrically conductive liquid is constantly present in the tissue and in the region of the tissue to be treated or treated, preferably at the distal end of the bipolar electrosurgical instrument, as a result of which the tissue coagulation by means of the electrosurgical instrument is improved overall.

A further advantage of the present disclosure is that, due to the provision and feeding of liquid in the region of the object to be treated or treated, in particular of the biological tissue, sufficient liquid is present during the treatment. This makes it possible, for example, to reduce the application time of the electrosurgical instrument during the treatment with a higher average performance of the high-frequency generator. Furthermore, by means of the electrosurgical system disclosed herein it is possible to treat larger coagulation zones in the case of biological tissue.

Due to the dosed and/or controlled conveyance of a quantity of liquid to the distal end of the shaft of the bipolar electrosurgical instrument and following the passage of the quantity of liquid out of the shaft through the at least one outlet opening at the distal end of the shaft into the region of the object to be treated, in particular of the biological tissue, this region of the object is supplied with a conditioning fluid at the distal end of the shaft of the bipolar electrosurgical instrument such that a sufficient or optimal quantity of liquid is provided in the region of the treatment zone of the instrument.

In this case, the quantity of liquid is introduced into the treatment region in a controlled manner at the distal end of the shaft into the object. In particular, liquid or the quantity of liquid is fed in the case of a bipolar instrument into the treatment region between the electrodes since a higher or the highest current density occurs between the electrodes.

The impedance of the object, in particular of the biological tissue, or the tissue impedance is measured by means of the impedance measuring device, wherein a corresponding signal is given to the liquid feeding device by means of the control device connected to the impedance measuring device such that in the event of too high an impedance value, a predetermined quantity of liquid is conveyed into the treatment region of the distal end of the electrosurgical instrument or is introduced into said region. It is for example ascertained by means of the control device that, during a measurement, the measured actual impedance value exceeds a predetermined nominal impedance value such that a corresponding signal is subsequently sent to the liquid feeding device, as a result of which the liquid feeding device introduces a predetermined quantity of liquid into the object region or tissue region to be treated.

The impedance measuring device is designed in order to measure the impedance of the tissue in the vicinity or in the region of the distal end of the shaft. The impedance measuring device is preferably configured in the high-frequency generator with a first electrode and second electrode of the bipolar electrosurgical instrument.

In particular, the outlet opening for the quantity of liquid at or in an insulator is configured between the first electrode and the second electrode of the electrosurgical instrument at the distal end of the shaft. In particular, the quantity of liquid is dispensed at the proximal end of the insulator between a first electrode on the distal side and a second electrode on the proximal side into the object to be treated, in particular biological tissue, via the at least one outlet opening.

Due to the feeding of the quantity of liquid into the object to be treated, in particular biological tissue, a conditioning medium is introduced in this region. A medium or a conductive liquid for stabilizing the impedance during a HF application (high-frequency application) of the bipolar electrosurgical instrument in the tissue is provided by the conditioning medium.

A further embodiment of the electrosurgical instrument is distinguished by the fact that the liquid feeding device has a liquid reservoir for providing a liquid and a conveying device for conveying a quantity of liquid from the liquid reservoir to the distal end of the shaft of the bipolar electrosurgical instrument. As a result, the corresponding quantity of liquid is dispensed in a dosed and/or controlled manner into the surroundings of the distal end of the shaft.

In addition, it is advantageous that the liquid feeding device and/or the liquid reservoir is/are connected via a conveyor line to the at least one outlet opening at the distal end of the shaft of the bipolar electrosurgical instrument.

In addition, a further embodiment of the electrosurgical system is characterized in that a cooling device for cooling the distal end of the shaft of the bipolar electrosurgical instrument is provided.

The fact that, in addition to the conditioning of the tissue to be treated by means of the quantity of liquid conveyed to the distal end of the shaft, the distal end is also cooled by means of the cooling device means that the applicability or the utilization application of the electrosurgical system is improved overall. The electrosurgical system is distinguished by the fact that separate channels in particular are provided for the cooling as well as for the quantity of liquid provided for the conditioning. An open cooling system is preferably provided by means of the cooling device.

In an advantageous embodiment, it is moreover provided that the cooling device has a cooling line in the interior of the shaft.

In particular, the cooling device having the cooling line is configured as an open cooling system for the electrosurgical system, in which a cooling fluid, e.g., water, is extracted from a reservoir, which is conveyed by the cooling line in the interior of the shaft and is carried away following cooling of the shaft and passage out of the shaft, i.e., it is not returned to the cooling line again.

It is additionally advantageous in the case of the electrosurgical system that a liquid line for the quantity of liquid conveyed by the liquid feeding device, which is separate with respect to the cooling line, is arranged in the interior of the cooling line, wherein the liquid line is guided out of the cooling line at the distal end of the shaft. In particular, the cooling device makes it possible for a constant cooling volume flow to be provided in order to cool the distal end of the shaft, wherein a variable liquid mass flow or conditioning volume flow is additionally provided by the control of the liquid feeding device by means of the control device as a function of the impedance measurement performed by the impedance measuring device.

It is furthermore provided according to a further embodiment of the electrosurgical system that the first electrode and the second electrode are arranged spatially separated from one another and electrically insulated at the distal end of the shaft of the bipolar electrosurgical instrument. In particular, an insulator with at least one outlet opening for the quantity of liquid introduced for conditioning the biological tissue to be treated from the interior of the shaft of the bipolar electrosurgical instrument is provided between the first and the second electrode.

Furthermore, the object is achieved by a method for operating an electrosurgical instrument, as described above. In order to avoid repetitions, reference is expressly made to the explanations above. During, e.g., a tissue coagulation of a biological tissue, a saline solution is in particular introduced as a liquid by the liquid feeding device. In particular, the saline solution has a concentration of 0.9% NaCl.

Further features will become evident from the description of embodiments, together with the claims and the appended drawings. Embodiments can fulfil individual features or a combination of multiple features.

Within the context of the disclosed features which are labeled with "in particular" or "preferably" are to be understood to be optional features.

BRIEF DESCRIPTION OF THE DRAWINGS

The present disclosure will be described below without limiting the general concept of the present disclosure by means of exemplary embodiments with reference to the drawings, wherein reference is expressly made to the drawings regarding all of the details according to the disclosure which are not explained in greater detail in the text, wherein.

DETAILED DESCRIPTION

Figure 1:
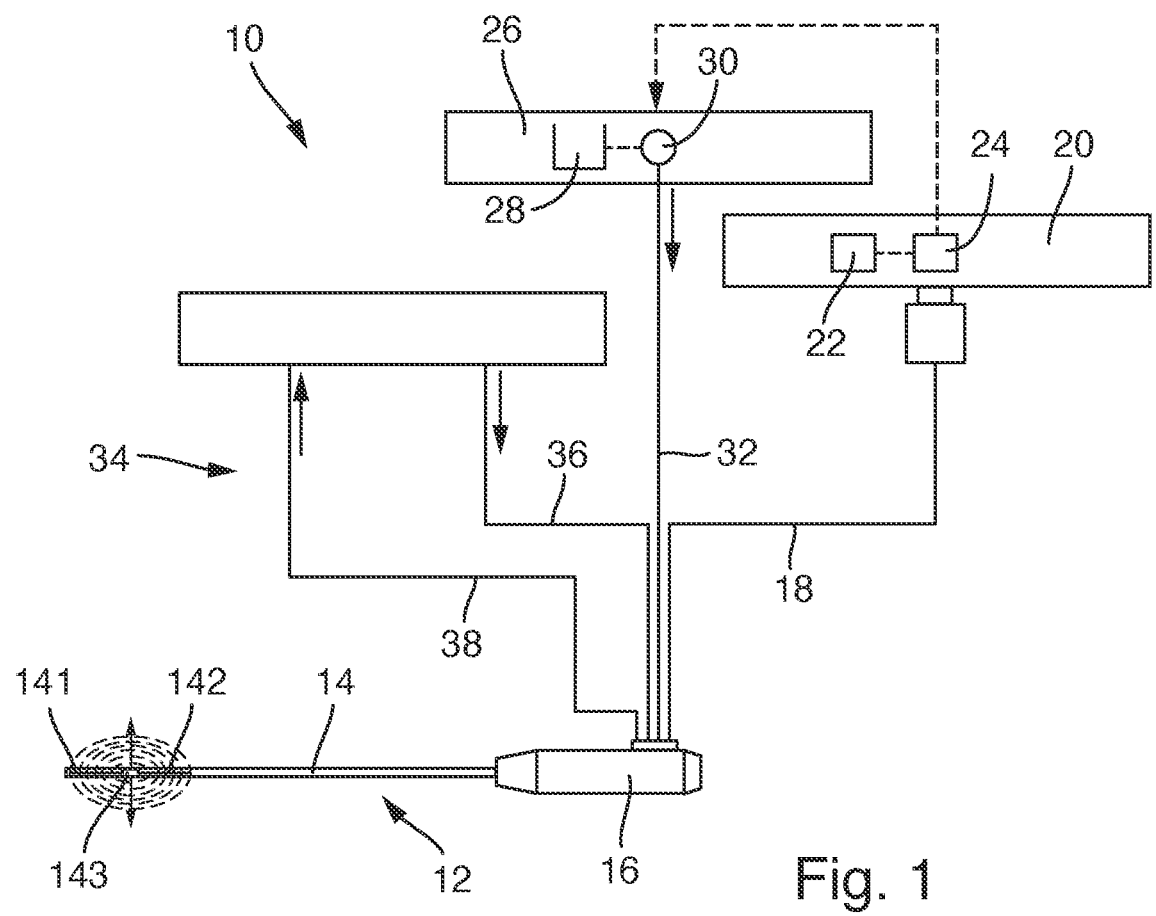
FIG. 1 schematically shows an exemplary configuration of an electrosurgical system according to the present disclosure, and FIG. 2 schematically shows a cross-section through a shaft of a bipolar electrosurgical instrument at the distal end of the shaft.

In the drawings, the same or similar elements and/or parts are, in each case, provided with the same reference numerals such that they are not introduced again in each case.

In FIG. 1, a circuit diagram of an electrosurgical system 10 is depicted schematically. The electrosurgical system 10 comprises a bipolar electrosurgical instrument 12 having an elongated or longitudinally extended shaft 14. Furthermore, the bipolar electrosurgical instrument 12 has a handle 16 arranged at the proximal end of the shaft 14. A first electrode 141 and a second electrode 142 are configured at the distal end of the shaft 14.

The two electrodes 141, 142 are arranged behind one another in the axial direction of the shaft 14, wherein the two electrodes 141, 142 are electrically insulated from one another. To this end, an insulator 143 is arranged between the distal electrode 141 and the proximal electrode 142.

The electrodes 141, 142 are each connected to the high-frequency generator 20 via separate electrical conductors (not depicted here), which are guided in a connecting line 18 outside of the bipolar electrosurgical instrument 12 from the handle 16 to a high-frequency generator 20 of the electrosurgical system 10. The electrical conductors for the electrodes 141, 124 are each connected at the ends to connecting contacts of the high-frequency generator 20.

The high-frequency generator 20 has an impedance measuring device 22 in order to measure the impedance of the tissue, into which the distal tip of the electrosurgical instrument 12 having the electrodes 141, 142 is introduced. The impedance measuring device 22 is additionally connected to a control device 24 of the high-frequency generator 20 in order to give corresponding control signals in the event of deviations from predetermined nominal impedance values to a liquid feeding device 26 of the electrosurgical system 10, which is connected to the control device 24. The control device 24 may be a processor or controller, such as a central processing unit (CPU).

The liquid feeding device 26 has a liquid container 28, from which a liquid, such as e.g., a saline solution, is pumped by means of a conveyor pump 30 into a supply line 32. The supply line 32 is connected to the bipolar electrosurgical instrument 12 such that the quantity of liquid pumped from the container 28 is conveyed via the separate supply line 32 within the shaft 14 to the distal tip of the shaft 14 of the electrosurgical instrument 12, wherein the quantity of liquid conveyed to the distal end of the shaft 14 is introduced via a corresponding opening into the surroundings between the two electrodes 141, 142 (cf. FIG. 2).

In order to cool the distal end of the shaft 14 of the electrosurgical instrument 12 during operation of the high-frequency generator 20, a closed cooling circuit 34 for the electrosurgical instrument 12 is additionally provided. The cooling circuit 34 has a feed line 36 in order to convey a cooling medium such as, e.g., water, to the distal end of the shaft 14 within the electrosurgical instrument 12. The cooling medium fed back from the bipolar electrosurgical instrument 12 is fed back via a corresponding return line 38.

Figure 2:
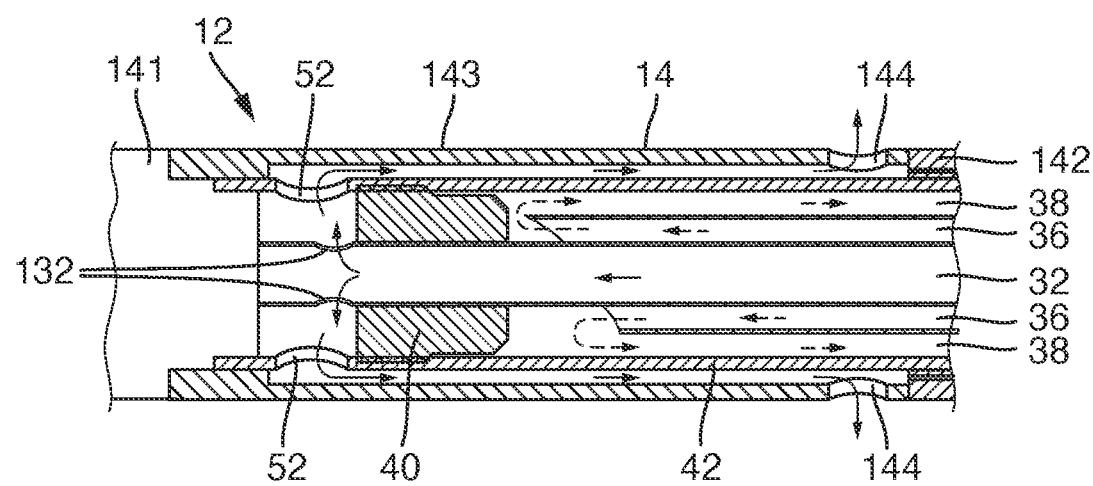

The distal end of the shaft 14 is depicted schematically in FIG. 2 in a schematized representation in the segment. In the interior of the shaft 14, the supply line 32 is arranged within the feed line 36 which is configured as a cooling line. As a result, the cooling circuit having the feed line 36 and the return line 38 is guided separately from the supply line 32 within the shaft 14.

The feed line 36 is open towards the distal end of the shaft 14. A seal 40 for the cooling medium, which seals off the inner shaft pipe 42, is provided at the end of the feed line 36 within an inner shaft pipe 42 such that the cooling medium, which is conveyed through the feed line 36 to the distal tip of the shaft 14, is diverted at the seal 40 in order to feed back the cooling medium conveyed in the feed line 36 in the region between the inner shaft pipe 42 and the feed line 36 to the proximal end of the shaft 14 in the return line 38.

The supply line 32 arranged in the interior of the coolant line 36 is guided through the seal 40 in the inner shaft pipe 42 in the center, wherein lateral openings 132 are provided at the end of the supply line 32 such that the liquid conveyed from the container 28 can pass out. The shaft pipe 42 has, in the region of the openings 132 of the supply line 32, outlet openings 52 such that the liquid is subsequently conveyed through the outlet openings 52 of the inner shaft pipe 42.

A channel is configured between the inner shaft pipe 42 and the outer sleeve-type insulator 143, which is arranged between the electrodes 141, 142, such that the liquid is conveyed through from the supply line 32 into said channel between the inner shaft pipe 42 and the outer sleeve-type insulator 143.

At the end, at the proximal end of the insulator 143, the latter has at least several outlet openings 144 such that the liquid passes out of the supply line 32 via the outlet openings 144 into the surroundings between the first electrode 141 and the second electrode 142. As a result, for example, when the distal end of the shaft 14 is arranged in a biological tissue, the liquid is introduced from the supply line 32 in a dosed and/or controlled manner on the basis of the control circuit according to the present disclosure, as a result of which the tissue impedance can be maintained within a predetermined region.

If, for example, an exceeding of the tissue impedance (actual impedance value) measured by the impedance measuring device 22 by a nominal impedance value is ascertained, the conveyor pump 30 is activated by the control device 24 such that a predetermined quantity of liquid is introduced by the liquid feeding device into the tissue between the electrodes 141, 142.

All of the indicated features, including those which are to be inferred from the drawings alone, and individual features which are disclosed in combination with other features, are deemed to be essential to the disclosure both alone and in combination. Embodiments may be performed by individual features or a combination of multiple features.

LIST OF REFERENCE NUMERALS

10 Electrosurgical system
12 Bipolar electrosurgical instrument
14 Shaft
16 Handle
18 Connecting line
20 High-frequency generator
22 Impedance measuring device
24 Control device
26 Liquid feeding device
28 Container
30 Pump
32 Supply line
34 Cooling circuit
36 Feed line
38 Return line
40 Seal
42 Inner shaft
52 Outlet opening
132 Opening
136 Opening
141 Electrode
142 Electrode
143 Insulator
144 Outlet opening

The invention claimed is:

1. An electrosurgical system comprising:
a bipolar electrosurgical instrument including:
an elongated shaft with a proximal end and a distal end, the distal end of the elongated shaft including at least one outlet opening, and
a first electrode and a second electrode that are provided at the distal end of the elongated shaft, the first electrode being connected to a first electrical conductor and the second electrode being connected to a second electrical conductor,
a high-frequency generator including:
a first output contact that can be or is connected to the first electrical conductor of the bipolar electrosurgical instrument, and
a second output contact that can be or is connected to the second electrical conductor of the bipolar electrosurgical instrument, and
a liquid feeding device configured to feed a quantity of liquid to the distal end of the elongated shaft such that the quantity of liquid passes through the at least one outlet opening at the distal end of the elongated shaft,
wherein the high-frequency generator further includes:
an impedance measuring device configured to measure a tissue impedance of the high frequency generator, and
a control device that is connected to the impedance measuring device and the liquid feeding device and is configured to control and/or dose the quantity of liquid fed by the liquid feeding device to the distal end of the elongated shaft as a function of a measurement of the tissue impedance of the high frequency generator,
wherein the control device is configured to stabilize the tissue impedance by providing a metered amount of the liquid, the liquid being a conductive liquid.

2. The electrosurgical system according to claim 1, wherein the liquid feeding device includes a liquid reservoir for storing the liquid and a conveying device configured to convey the quantity of liquid from the liquid reservoir to the distal end of the elongated shaft.

3. The electrosurgical system according to claim 2, wherein at least one of the liquid feeding device and the liquid reservoir is connected via a conveyor line to the at least one outlet opening at the distal end of the elongated shaft.

4. The electrosurgical system according to claim 3, wherein the at least one outlet opening at the distal end of the shaft is configured on a hollow needle.

5. The electrosurgical system according to claim 1, further comprising a cooling device configured to cool the distal end of the elongated shaft.

6. The electrosurgical system according to claim 5, wherein the cooling device includes a cooling line disposed in an interior of the elongated shaft.

7. The electrosurgical system according to claim 6, further comprising a liquid line for delivering the quantity of liquid conveyed by the liquid feeding device, the liquid line being separate from the cooling line and being arranged in the interior of the cooling line, wherein the liquid line is guided out of the cooling line at the distal end of the elongated shaft.

8. The electrosurgical system according to claim 1, wherein the first electrode and the second electrode are arranged spatially separated from one another and electrically insulated at the distal end of the elongated shaft.

9. The electrosurgical system according to claim 1, wherein the at least one outlet opening is disposed in between the first electrode and the second electrode along a longitudinal axis of the elongated shaft.

10. The electrosurgical system according to claim 1, wherein the elongated shaft further includes an insulator arranged between the first electrode and the second electrode along a longitudinal axis of the elongated shaft, and the at least one outlet opening is formed in a wall of the insulator.

11. A method for operating the electrosurgical system according to claim 1, the method comprising:
measuring the tissue impedance of the high frequency generator, and
delivering the liquid from the liquid feeding device through the at least one outlet opening at the distal end of the elongated shaft as a function of the measurement of the tissue impedance.

* * * * *